(12) United States Patent
Seidel-Morgen-Stern et al.

(10) Patent No.: US 7,820,860 B2
(45) Date of Patent: Oct. 26, 2010

(54) METHOD FOR SEPARATING COMPOUND-FORMING CHIRAL SYSTEMS

(75) Inventors: Andreas Seidel-Morgen-Stern, Magdeburg (DE); Heike Lorenz, Magdeburg (DE); Daniel Polenske, Egeln (DE)

(73) Assignee: Max-Planck-Gesellschaft Zur Forderung Der Wissenshaften E.V., Egeln (DE)

( * ) Notice: Subject to any disclaimer, the term of this patent is extended or adjusted under 35 U.S.C. 154(b) by 0 days.

(21) Appl. No.: 12/064,329

(22) PCT Filed: Aug. 17, 2006

(86) PCT No.: PCT/EP2006/065413
§ 371 (c)(1),
(2), (4) Date: Feb. 20, 2008

(87) PCT Pub. No.: WO2007/023129
PCT Pub. Date: Mar. 1, 2007

(65) Prior Publication Data
US 2008/0207944 A1    Aug. 28, 2008

(30) Foreign Application Priority Data
Aug. 20, 2005  (DE) .................. 10 2005 039 501

(51) Int. Cl.
*C07C 51/42* (2006.01)
(52) U.S. Cl. .................................... 562/600
(58) Field of Classification Search ........... None
See application file for complete search history.

(56) References Cited

U.S. PATENT DOCUMENTS 5,260,482 A    11/1993   Pringle et al.

FOREIGN PATENT DOCUMENTS

| DE | 19536827 A1 | | 4/1997 |
|---|---|---|---|
| EP | 0220435 | * | 5/1978 |
| EP | 0220435 A1 | | 5/1987 |
| JP | 60202853 | * | 10/1985 |
| JP | 60202853 A | | 10/1985 |
| WO | 199508522 A1 | | 3/1995 |
| WO | 2007023129 A3 | | 3/2007 |

OTHER PUBLICATIONS

"Pharmaceuticals, Chiral" in Kirk Othmer Encyclopedia of Chemical Technology, Copyright © 1996 by John Wiley & Sons, Inc., Article Online Posting Date: Dec. 4, 2000, pp. 1-49.*

Polenske, D, et al. (2006) Alternative Einsatzmoglichkeiten der "Bevorzugten Kristallisation" zur Enantiomerentrennung. Chemie Ingenieur Technik, 78(8):1101-10.

Elsner, M., et al. (2005) Experimental Study and Simplified Mathematical Description of Preferential Crystallization. Chirality, 17:S183-95.

Perlberg, A., et al. (2005) Crystal Growth Kinetics via Isothermal Seeded Batch Crystallization: Evaluation of Measurement Techniques and Application to Mandelic Acid in Water. Ind. Eng. Chem. Res., 44(4):1012-20.

Lorenz, H., et al. (2002) Enantiomeric Mandelic Acid System-Melting Point Phase Diagram and Solubility in Water. J. Chem. Eng. Data, 47(5):1280-84.

(Continued)

*Primary Examiner*—Karl J Puttlitz

(57) ABSTRACT

Methods for racemate separation for compound-forming substances. In this method, at least one fraction which is enriched with an enantiomer is produced in one method step. Finally, a preferred crystallization is carried out on the fraction.

11 Claims, 4 Drawing Sheets

OTHER PUBLICATIONS

Rodrigo, A., et al. (2004) Online Monitoring of Preferential Crystallization of Enantiomers. Chirality, 16:499-508.

van der Ent, E.M., et al. (2001) Design criteria for dense permeation-selective membranes for enantiomer separations. Journal of Membrane Science, 185:207-21.

Sheehan, P., et al. (2000) Zur Kopplung von Chromatographie and Kristallisation zur Trnnung von Enantiomeren. Chemie Ingenieur Technik, 72:940-41.

Grandeury, A., et al. (2003) Crystallization of Supramolecular Complexes as an Alternative Route for the Separation of Racemic p-X-Phenylethanol. Chem. Eng. Technol, 26(3):354-58.

Elsner, M., et al. (2004) Die Bevorzugte Kristallisation zur Auftrennung von racemischen Gemischen. Chemie Ingenieur Technik, 76(9):S138.

Lorenz, H., et al. (2001) Theoretical and Experimental Study of Thermodynamic and Kinetic Aspetcs of Enantioselective Crystallization. Chemie Ingenieur Technik, 73(6):712.

\* cited by examiner

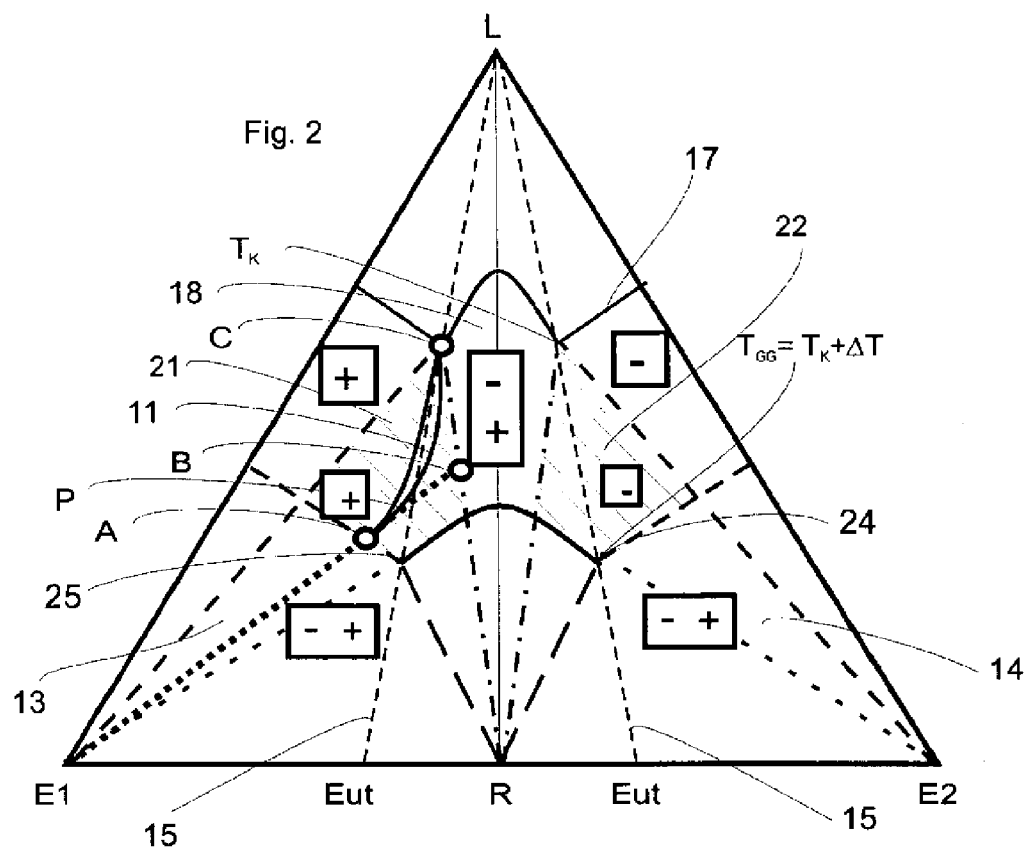
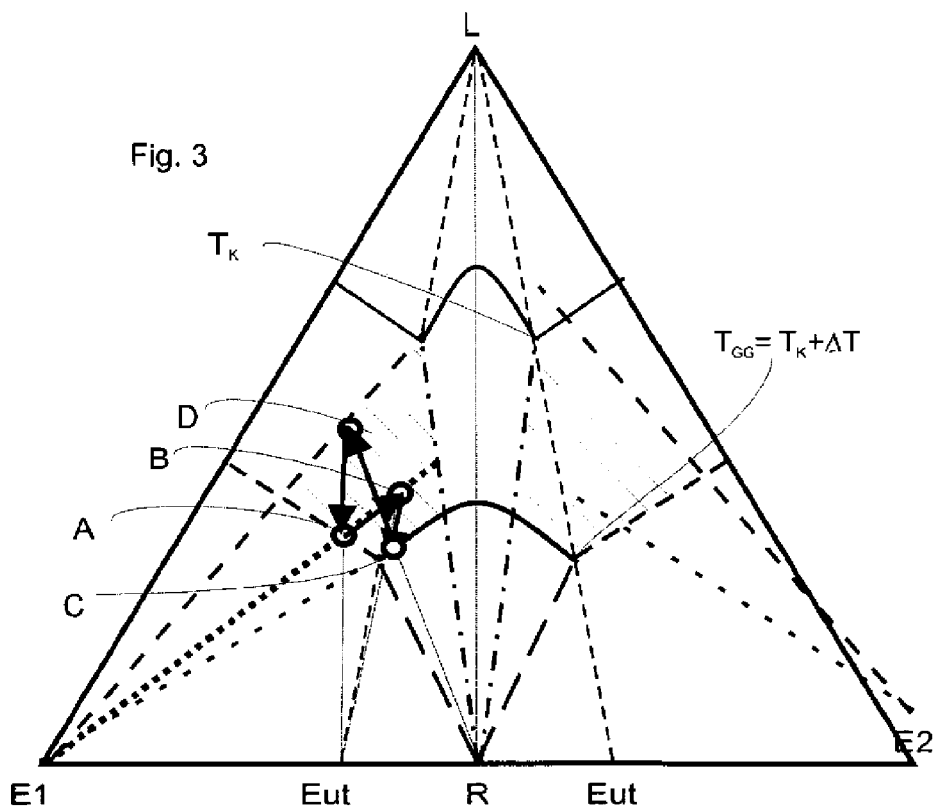

METHOD FOR SEPARATING COMPOUND-FORMING CHIRAL SYSTEMS

PRIORITY CLAIM

This application is a 35 U.S.C. §371 filing of PCT/EP2006/065413 which claims priority to German Patent Application Ser. No. 10 2005 039 501.5 filed Aug. 20, 2005.

FIELD OF THE INVENTION

The present invention relates to a method for racemate separation in compound-forming systems.

BACKGROUND

A racemate is understood to mean an equimolar mixture of two enantiomers. Enantiomers are isomers, that is to say substances which do not differ with regard to the overall formula but rather only in the arrangement of the atoms. In the case of enantiomers, the difference lies in the chirality, i.e. in the property of behaving like an image and mirror image relative to one another.

A separation of these racemic mixtures, which will be referred to below as racemate separation, is usually difficult since the chemical and physical properties of the enantiomers are identical apart from their behavior in relation to linearly polarized light and other chiral substances.

Many pharmaceutically active substances are chiral. Often, however, only one of the two enantiomers can be used as an active substance since the physiological effects of the enantiomers on the human organism usually differ from one another. In addition, the obtaining of pure enantiomers is also highly important in agrochemistry and in the food industry. The market for enantiomeric substances (in pharmaceutically active substances, plant protection agents, dyes and fragrance compounds) has increased considerably in recent years.

One method for racemate separation which is known from the prior art is referred to as preferred crystallization. However, according to the prior art, this method can be used only for so-called conglomerate-forming substance systems, i.e. for those systems in which the enantiomers are immiscible in the solid phase. On the contrary, preferred crystallization cannot to date be used for compound-forming substance systems, which are much more common.

Only around 5-10% of all chiral systems are conglomerate-forming systems, whereas most of the remaining systems are compound-forming systems. For thermodynamic reasons, these systems cannot be separated starting from the racemate by means of preferred crystallization.

Other possibilities for racemate separation are known from the prior art. These possibilities include e.g. chemical methods, in which firstly diastereomers are formed, biochemical methods, i.e. methods which are carried out using microorganisms or enzymes, or chromatographic methods. In general, preferred crystallization offers advantages over these methods.

SUMMARY OF THE INVENTION

The object of the present invention is therefore to provide a method for racemate separation of compound-forming chiral systems which is much simpler than the prior art. Another object is to provide a method which uses the method of preferred crystallization known from the prior art, which is itself a simple and inexpensive method.

According to the invention, this is achieved by a method according to claim 1. Advantageous further developments of the method form the subject matter of the dependent claims.

Method 1 according to the invention (FIG. 4) starts from a racemic mixture which is produced as a target product during chemical synthesis. In the first method step, the racemate is split by an enrichment step into at least one enriched fraction. In a further method step—preferred crystallization—the target enantiomer and/or racemate is obtained from the enriched fraction(s). The racemate can be passed back to the first method step as a starting substance. The racemate can thus be split into the two enantiomers via a cyclic process. No by-products are obtained.

As an alternative to this method, a second, more complex method can be proposed. In this case, a further method step—so-called (conventional) enantioselective crystallization—is incorporated between the two abovementioned method steps of the method. With enantioselective crystallization, relatively large enantiomeric excesses can be selectively crystallized out. The need for this method step depends on the first method step and on the phase diagram of the chiral substance. The mother liquors remaining at the end of enantioselective crystallization then contain the enantiomers in each case in a eutectic composition. In this modified method, at least one of the two target enantiomers is obtained in method steps II and III; furthermore, in a manner analogous to method 1, racemate is obtained as a by-product in method step II, which can be used as a starting substance in method step I.

According to the invention, therefore, a hybrid process is proposed which contains on the one hand an enrichment step and on the other hand the step of preferred crystallization. The reason for this is that, as mentioned above, the compound-forming substance systems cannot be separated starting from the racemate by means of preferred crystallization. If the mixture to be separated contains an enantiomeric enrichment which corresponds to or even exceeds the eutectic composition, the method principle of preferred crystallization can be used to obtain the desired enantiomer.

The enriched fraction is preferably produced by a chromatographic method. A chromatographic method allows the splitting of a substance mixture, since a weight of distribution is set between a stationary and a mobile phase. In another preferred variant, the enriched fraction is produced using an enantioselective membrane. Such membranes allow the passage of one enantiomer while preventing or reducing the passage of the other enantiomer, and in this way the respective enriched fractions are produced. The enriched fraction is preferably produced in a crystallization process using supramolecular complexes. In this case, the separation takes place according to the known guest/host principle.

As a result of the enrichment, usually two enriched fractions are obtained, wherein one fraction is enriched with an enantiomer E1 and the other is enriched with an enantiomer E2 above the eutectic composition. These enantiomeric excesses can be selectively crystallized, wherein the mother liquors remaining at the end of the crystallization processes contain the enantiomers in each case in eutectic composition.

During the preferred crystallization, the desired enantiomer and racemate are crystallized in a cyclic manner from an enantiomerically enriched sub-eutectic, eutectic or supereutectic mixture of an enantiomer and the racemate during one method step and are in each case separated out as a solid. The enriched fraction is seeded with the enantiomer to be separated or with the racemate in order thus to start the preferred crystallization. During the preferred crystallization, only the desired enantiomer or racemate is crystallized after seeding with the corresponding seed crystals.

The racemate produced in the process is preferably passed back to the racemic mixture which is required in the enrichment step (method step I).

In this way, an overall cyclic process can be carried out.

The preferred crystallization is stopped when the nucleation of the respectively undesired racemate or enantiomer occurs. It should be noted that, at least in the initial phase of preferred crystallization, predominantly or only the desired enantiomer or racemate is produced.

Individual method steps and in particular the method step of preferred crystallization are preferably monitored in an essentially continuous manner. In order to safely carry out the described crystallization processes, efficient analysis, i.e. continuous monitoring, is recommended. The individual method steps are monitored by a method selected from a group of methods comprising polarimetric measurements, density measurements, refractometric measurements and the like and also combinations of these methods. As a result of this monitoring method, it is possible to ascertain for example the point in time at which the crystallization of the desired enantiomer must be stopped.

BRIEF DESCRIPTION OF THE DRAWINGS

Further advantages and embodiments will emerge from the appended drawings.

In the drawings:

FIG. 2 is a phase diagram of a compound-forming system for a batch process;

FIG. 3 is a phase diagram of a compound-forming system for a cyclic process;

DETAILED DESCRIPTION OF THE PREFERRED EMBODIMENT

Figure 1A:
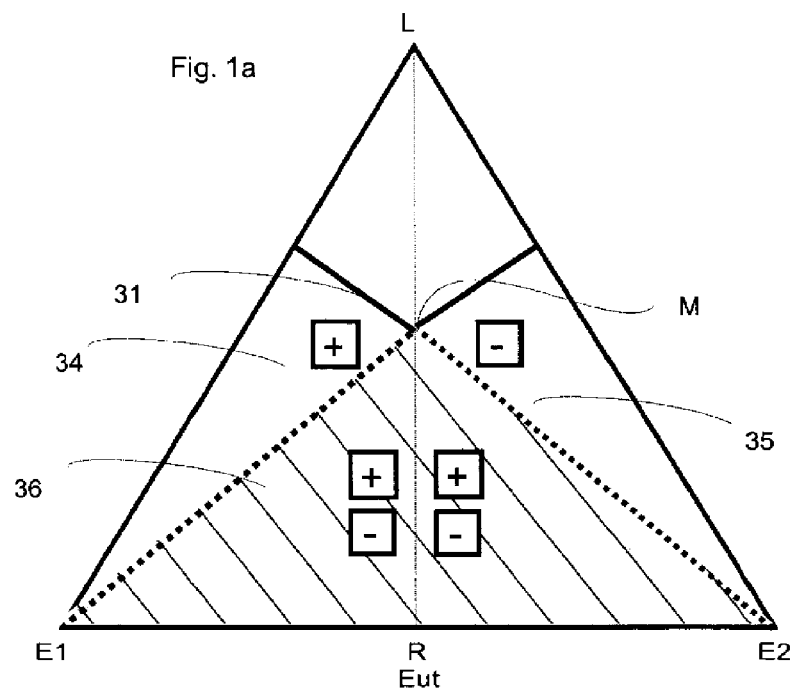
FIG. 1(a) is a ternary phase diagram of a conglomerate-forming system.

One important prerequisite for crystallization-based separation in ternary substance systems is to know the associated solid/liquid phase equilibrium. In the case of the chiral systems which form the subject matter here, two types of phase diagram are of particular importance, namely on the one hand the so-called conglomerate-forming systems, such as threonine/water for example, and on the other hand the compound-forming substance systems, such as mandelic acid/water. For illustration purposes, FIG. 1a shows a ternary phase diagram for conglomerate-forming substance systems and FIG. 1b shows a ternary phase diagram for compound-forming substance systems.

The solubility isotherm 31 for conglomerate-forming substance systems has in the ternary phase diagram for the racemic composition a maximum solubility which is marked by the point M. Here, the racemate corresponds to the eutectic mixing ratio of the enantiomers, which is marked by the abbreviation Eut. As shown in FIG. 1a, the area below the solubility isotherm can be divided into three further phase areas, namely into two two-phase areas 34, 35 and one three-phase area 36. For the preferred crystallization, only the three-phase area 36 is of interest here.

Figure 1B:
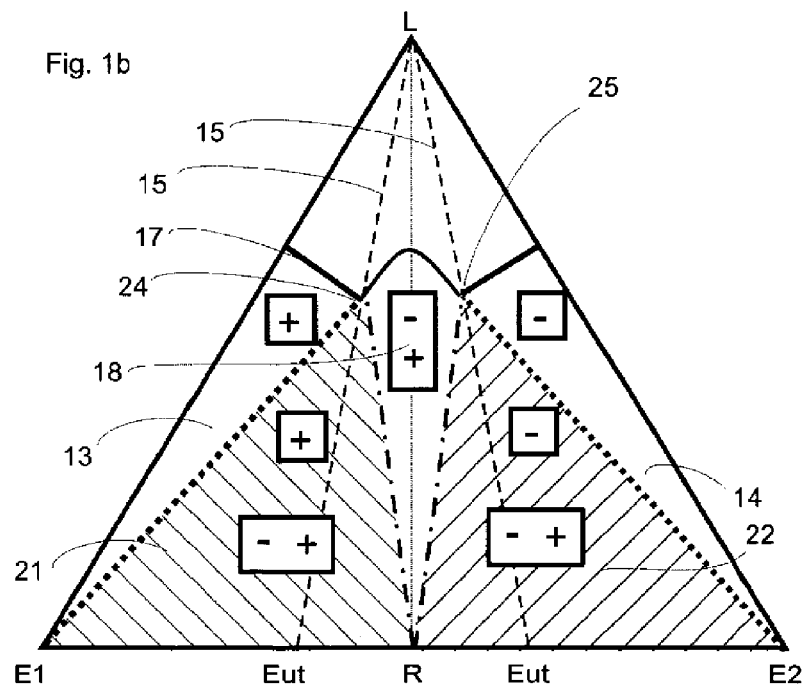
FIG. 1(b) is a ternary phase diagram of a compound-forming system.

FIG. 1b shows the phase diagram of a compound-forming system. The dashed lines 15, which run from the binary eutectic compositions (Eut) to the top corner point of the triangular diagram (solvent L), represent the so-called eutectic lines. Reference R on the bottom edge of the diagram denotes the racemic composition. The solubility isotherm 17 of compound-forming chiral systems has 5 marked solubility points (enantiomer, racemate and 2 eutectics).

Compound-forming substance systems are characterized in that, in the racemic composition, an intermediate compound (a racemic compound) is formed, and therefore maximum solubilities occur on both sides of the racemic compound in each case at the points of intersection of the solubility curves of enantiomer and racemate 24, 25. Due to the particular feature that an intermediate compound is produced, the area below the solubility isotherm can be divided into a total of five phase areas, namely three two-phase areas 13, 14, 18 and two three-phase areas. The three-phase areas, which in FIG. 1b are provided with the references 21 and 22 and are in each case defined by the corner point E1 or E2, the point R and the points 24 and 25, are characterized by the existence of a saturated solution, crystals of the compound and of one of the two enantiomers, i.e. of the enantiomer E1 in the case of area 21 and of the enantiomer E2 in the case of area 22. These regions are of interest for the preferred crystallization, since enantiomer E1 or E2 can be obtained from the solution.

The composition of the enantiomers at the point of the respective maximum solubility is substance-specific and also solvent- and temperature-dependent in the ternary phase diagram. The composition often corresponds to the eutectic mixing ratio in the chiral binary system, i.e. a eutectic line is formed.

With reference to FIG. 2, the principle of preferred crystallization will be described based on the batchwise crystallization of a compound-forming substance system. At the start of crystallization, indicated here by the point A, a saturated solution exists at TGG. This can be produced by the enrichment steps mentioned above. This saturated solution may be a eutectic mixture of the two enantiomers or may comprise an enantiomeric excess, such as e.g. at the point A in FIG. 2.

By cooling the solution, an over saturation is then produced. The extent of cooling $\Delta T$ is selected such that the point A remains within the width of the metastable region 21 (grey, dotted). In this way, spontaneous nucleation can be avoided. In the case of this spontaneous nucleation, no separation would take place.

If the solution thus oversaturated is seeded with crystals of an enantiomer, such as the enantiomer E1 in the case of the point A, then the crystallization, ideally only the crystallization of the enantiomer E1, would run along the line A→B. In actual fact, however, the process does not run along the line A→B but rather along the curved line A→C. The ideal asymptote in this curved line A→C is shown by the straight line A→B. As can be seen in the line or trajectory 11, the crystallization still runs along the line A→B at least in the initial phase, i.e. the enantiomer E1 crystallizes out with preference in this initial phase while the racemic compound R remains in solution. From a certain point in time onwards, the curved line 11 increasingly deviates from the ideal asymptote A→B, which means that now the racemate also crystallizes.

For the enantiomer separation, use is made of the fact that essentially only the enantiomer crystallizes up to a certain point in time. More specifically, the crystallization is stopped when the line A→C starts to deviate too greatly from the ideal line A→B. Permanent process monitoring is thus necessary for this process so as to ascertain the current stage of the process.

The enantiomer E2 could be crystallized in the same way on the right-hand side of the diagram along a corresponding path.

TGG denotes the equilibrium temperature and TK denotes the crystallization temperature.

FIG. 3 illustrates, in a further three-phase diagram, a cyclic process, which can be developed from the batchwise crystallization described above. In this case, two batchwise crystallization steps are carried out in one complete cycle. The first operating step (A→B) corresponds to the batch process shown in FIG. 2. Before the second part can be started, however, eutectic mixture must be added as the starting substance or feed (B→C).

At the start of the second operating step from point C to point D, seeding with crystals of the racemate takes place. At the respective target points B and D, crystallisate is separated out in each case, i.e. enantiomer E1 in the case of point B and racemate in the case of point D. In addition, preferably in each case eutectic mixture is added as the starting substance or feed.

On the whole, therefore, an enantiomer E1 and racemate can be obtained in a cyclic manner from the eutectic mixture by means of this cyclic process. As mentioned above, the enantiomeric enrichment of the starting substance or feed for the preferred crystallization may also exceed the eutectic composition.

Figure 4:
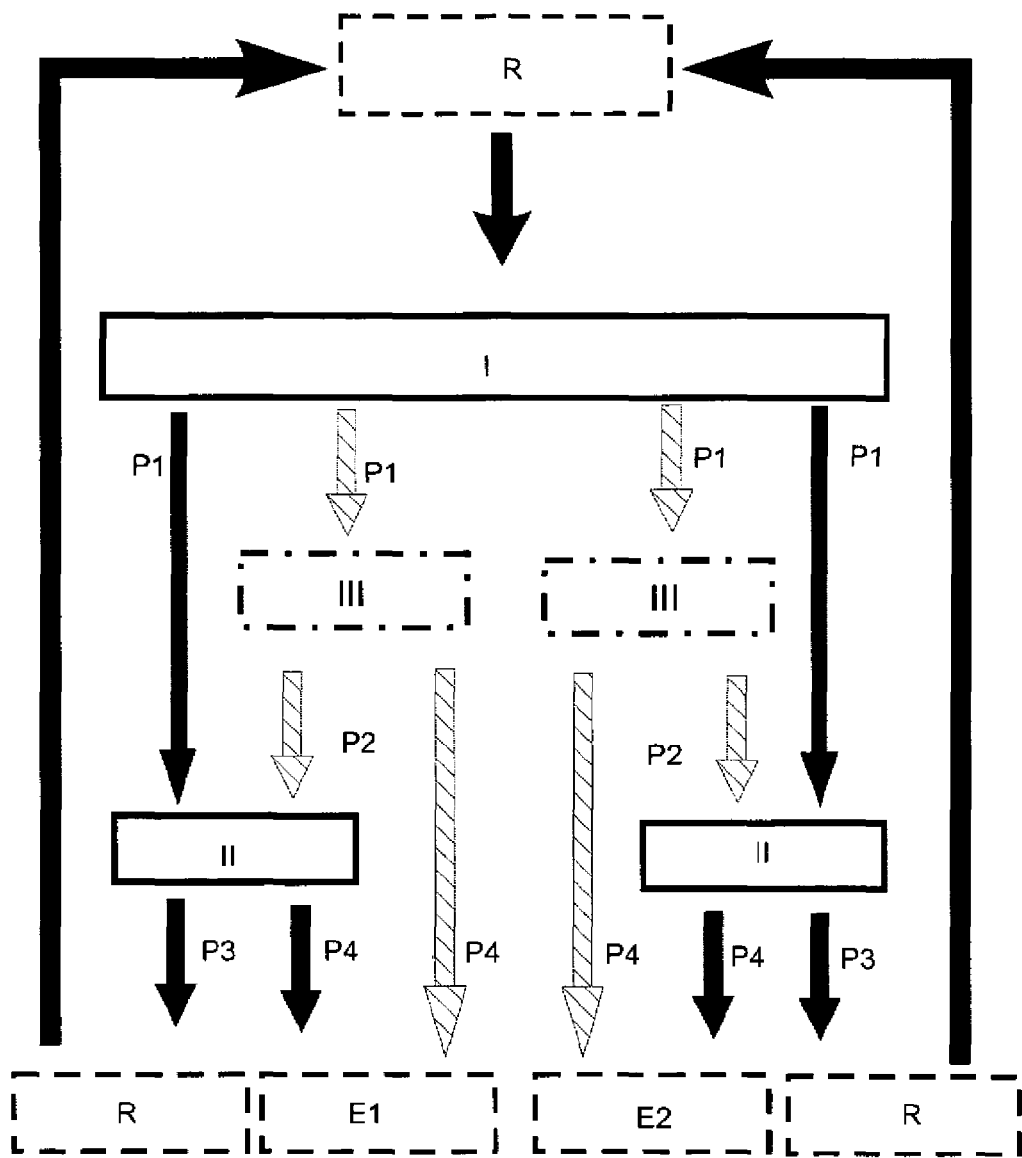
FIG. 4 is a block diagram of a hybrid process according to the invention.

FIG. 4 shows, in a block diagram, the possible method according to the invention. Starting from a racemate R, an enrichment step I is carried out such as, for example, the above-described chromatography. The enrichment step leads on the one hand to an enriched solution containing enantiomer E1 on the left-hand side along the left-hand arrow P1, and to a solution enriched with enantiomer E2 on the right-hand side along the right-hand arrow P1. The solution is then oversaturated for example by evaporation.

In the second method step (II)—the preferred crystallization—the target enantiomer and the racemate are obtained from the enriched fractions, along P4 and P3 respectively. As an alternative, an enantioselective crystallization (III) may be carried out before method step II (the preferred crystallization).

The mother liquors remaining at the end of the enantioselective crystallization contain the enantiomers in each case in eutectic composition (P2), and can be processed by means of the described process of preferred crystallization, whereby it is possible to obtain the pure enantiomers and the racemate as illustrated by the respective arrows P4 and P3. The racemate may be passed back to the initial step of enrichment, for example chromatographic enrichment.

As mentioned above, the advantage of the method according to the invention lies in the fact that crystallization-based methods can also be used to obtain pure enantiomers in compound-forming systems. As a result, in addition to the previous 5-10% conglomerate-forming systems, the remaining 90-95% chiral substances are also suitable for a simple and inexpensive crystallization-based enantiomer separation. Furthermore, under some circumstances, the method can also be used on very rare systems exhibiting complete miscibility in the solid phase.

In the case of mixed crystal formation, in general only a limited purity can be achieved in the crystallization-based separation method. The use of the method according to the invention is thus dependent on the purity to be achieved, which is defined for example by the purity requirements set by industry, and must be tested accordingly.

At the end of the coupled hybrid process, no residual mother liquors are left. As in the case of the direct crystallization of conglomerate-forming chiral systems, the racemate can be split into the two enantiomers.

In addition to the novel method described here, the described preferred crystallization can also be used accordingly to process eutectic mother liquors (from the solution and melt), resulting in a considerable economic potential. Eutectic residual mother liquors occur for example in the conventional enantioselective crystallization of compound-forming substance systems. They are still enriched to a certain degree with the target enantiomer, which makes it beneficial to carry out further processing and allows a corresponding increase in product yield and/or productivity.

EXAMPLES

The experiments were carried out in a 1.2 l temperature-controlled crystallization device using mandelic acid in water. The temperature was checked by a PT 100 resistance thermometer. The crystal-free solution, which had been separated using a standard HPLC filter, was pumped out of the crystallization device by means of a circulation pump. Flowing solution was analyzed by means of a polarimeter and a density-measuring device. Downstream of this test apparatus, the solution was sent back into the crystallization device by means of an insulated channel.

The crystallization conditions were selected according to the requirements for carrying out preferred crystallization, with the crystallization temperatures being between 10-30° C., the weight of the seed crystals being in the region of 2500 milligrams and the weight of the solution being in the region of 1000 g. The stirring speed was in the range between 300 and 400 revolutions per minute.

The experiments were carried out with different initial enantiomer contents. One pass was carried out with the solution composition between the racemic compound and the eutectic line, a second pass was carried out on the eutectic line and a third pass was carried out in a composition between the eutectic line and the enantiomer. The racemic compound was used as seed crystals. In the first case, as expected from the principle of preferred crystallization, the racemic compound crystallizes after seeding and the eutectic line is exceeded.

The second pass led to the same result, with the racemic component crystallizing above the eutectic line. In the above-mentioned third case as well, in which the starting point in the phase diagram is arranged on the side in which the enantiomer would preferably crystallize, a racemic compound is again obtained as a solid phase after seeding. Here, more or less pronounced chiral interactions in the oversaturated solution are responsible for these results.

Figure 5:
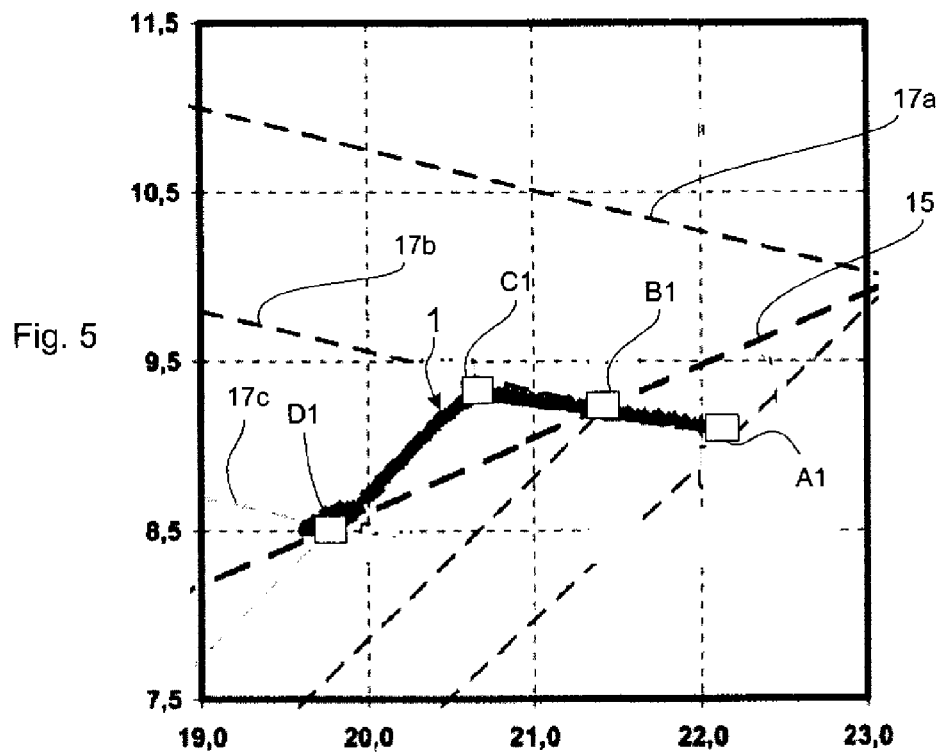
FIG. 5 is a quasi-binary phase diagram to illustrate the obtaining of pure enantiomer by means of preferred crystallization, based on the example of the mandelic acid/water system.
Figure 6:
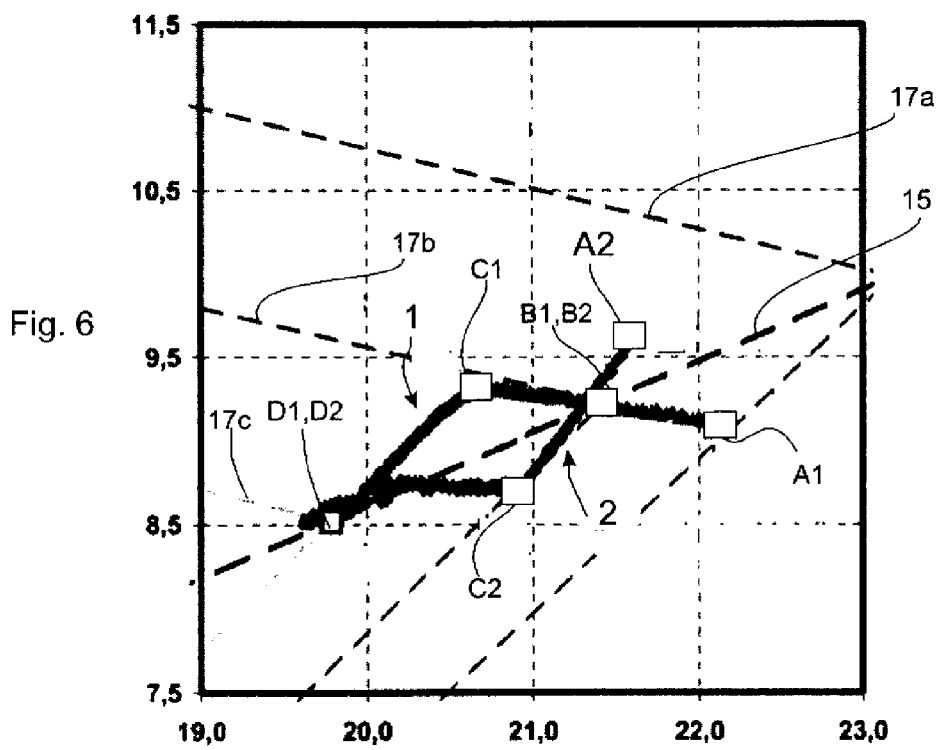
FIG. 6 is a quasi-binary phase diagram to illustrate a cyclic process based on the example of the mandelic acid/water system.

The above examples show the obtaining of racemic mandelic acid from solutions having an almost eutectic composition of the enantiomers (i.e. sub-eutectic, eutectic or supereutectic). FIGS. 5 and 6 show diagrams, which also show the possibility of obtaining pure enantiomer from mother liquids having a corresponding composition.

FIG. 5 shows a quasi-binary phase diagram for confirming the technical feasibility of obtaining pure enantiomer by means of preferred crystallization based on the example of the mandelic acid/water system. Here, the abscissa shows the amount by weight of (S)-mandelic acid in grams per 100 g of solution. The ordinate shows the amount by weight of (R)-mandelic acid, again in grams per 100 g of solution. FIG. 5 therefore shows an experiment in which the feasibility of obtaining pure enantiomer from a solution having an almost eutectic composition is shown.

In FIG. 5, reference 15 once again denotes the eutectic line and the lines 17a, 17b and 17c show solubility isotherms at 30° C., 29° C. and 28° C. respectively. In the experiment shown in FIG. 5, based on the example of the mandelic acid/water substance system, a 60 ml temperature-controlled crystallization device was used. The process monitoring took place in the manner described above. The crystallization temperature was 28° C. and the weight of solution was 50 g. The stirring speed was 400 revolutions per minute, and the quantity of seed crystals was 0.125 g. Seeding with the enantiomer was carried out. The oversaturation was 3.3 g/100 g of solution, and the enantiomeric excess was 41.5%.

References A1, B1, C1 and D1 denote process points.

At the start of the experiment shown in FIG. 5, as already mentioned, there was an oversaturated solution (Δc=3.3 g/100 g of solution) with an enantiomeric excess of 41.5% of (S)-mandelic acid. This is illustrated by the point A1. After seeding with (S)-mandelic acid seed crystals, (S)-mandelic acid crystallizes out with preference and the crystallization path in the quasi-binary phase diagram shown in FIG. 5 exceeds the eutectic line 15. This is illustrated at point B1, at which the enantiomeric excess is 40%.

As the process continues to point C1, pure enantiomer crystallizes and the enantiomeric excess reduces to approx. 37.9%. At this process point C1, nucleation of the undesired racemate occurs. If the crystallization process is not stopped at this point, the further crystallization between the process points C1 and D1 is characterized by a simultaneous crystallization of (S)- and (RS)-mandelic acid crystals. In this case, the crystallization of the racemate is dominant.

The point D1 corresponds to the thermodynamic equilibrium; the crystallization process is terminated at this point.

Here too, therefore, the experiments were carried out with a solution composition between the eutectic line 15 and the enantiomer, again using crystals of the enantiomer. The enantiomer crystallizes after seeding and the eutectic line is exceeded, as expected according to the principle of preferred crystallization.

FIG. 6 shows a quasi-binary phase diagram to illustrate a cyclic process. A process with two experimental passes 1 and 2 is shown, wherein pass 1 is shown by the references A1, B1, C1 and D1 according to FIG. 5 and pass 2 is shown by the references A2, B2, C2, D2. As shown in FIG. 5, the first pass was carried out with a solution composition between the eutectic line and the enantiomer, wherein once again seed crystals of the enantiomer were used. As a result, the enantiomer crystallizes after seeding and the eutectic line is exceeded, as expected for preferred crystallization.

In the second pass 2, the process was started with an oversaturated solution (Δc=3.3 g/100 g of solution) with an enantiomeric excess of 38.5% of (S)-mandelic acid. This is indicated by process point A2. After seeding with crystals of the racemate, the compound crystallizes until the turning point of the trajectory is reached, which is shown by process point C2. At this point, the enantiomeric excess is approx. 41.8%.

In this pass, too, the eutectic line is exceeded in the same way as in the first pass described above, as illustrated by point B2. If the crystallization process is not stopped at process point C2, the enantiomer and the racemate crystallize simultaneously during the further crystallization, i.e. between the points C2 and D2, with the crystallization of the enantiomer being dominant at the start. In a manner corresponding to the experiment shown in FIG. 5, the thermodynamic equilibrium is reached at an enantiomeric excess of approx. 40%, which is illustrated by process point D2.

In the second pass 2, therefore, the crystallization was carried out with a solution composition between the racemic compound and the eutectic line, wherein here the racemate crystallizes after seeding with crystals of the racemic compound and the eutectic line is exceeded, as expected for the principle of preferred crystallization.

To sum up, in the method according to the invention, a selective crystallization is carried out despite thermodynamic limitation. The method according to the invention is based on the different crystallization rate of the enantiomer and of the racemic compound in an oversaturated solution in the presence of seed crystals of this enantiomer or the racemic compound, i.e. it is a kinetically driven separation. The use of the method according to the invention on compound-forming systems allows the processing of the residual mother liquors mentioned above and prevents the loss of useful material. By contrast, in the case of conventional enantioselective crystallization, only the excess of an enantiomer up to the eutectic composition is obtained (thermodynamic limitation), i.e. a residual mother liquor always remains which contains the enantiomers in eutectic composition.

Using the method according to the invention, therefore, chiral systems are separated from a solvent, i.e. in the ternary system. The starting point for this is a solution, which contains the two enantiomers in a eutectic or supereutectic composition.

Thermodynamically speaking, there is no "solution with a eutectic composition or eutectic mixture". The experiments carried out by the applicant have also shown that the preferred crystallization in the compound-forming system of mandelic acid is also possible even starting from solutions which contain the two enantiomers in a sub-eutectic composition. In other words, preferred crystallization can also be used in the case of an enantiomeric enrichment below the eutectic composition.

A combination of enantiomeric enrichment and preferred crystallization is therefore proposed, which allows recycling and thus further processing of the racemate obtained in a manner alternating with the pure enantiomer. It is also separated from the solvent, which is particularly important for organic substances which tend to break down at higher temperatures.

Use is therefore made of the fact that, if an upstream enantiomeric enrichment has taken place in the chiral system, the enriched enantiomer and the racemic compound can crystallize separately (there is a eutectic in the enantiomer/racemate half-diagram). This enantiomer and the racemic compound are obtained in a cyclic process, with the latter being recycled to the enrichment step by the process coupling system. In the case of enrichment of the other enantiomer, the preferred crystallization results in this enantiomer and the racemic compound. A corresponding coupled method can then result in the two enantiomers, with no residual mother liquors being obtained.

All the features disclosed in the application documents are claimed as essential to the invention in so far as they are novel individually or in combination with respect to the prior art.

LIST OF REFERENCES 1, 2 experimental pass
11 trajectory
13, 14, 18 two-phase areas
15 eutectic line
17 solubility isotherm 17a, 17b, 17c solubility isotherms (FIG. 5+FIG. 6)
21, 22 three-phase areas
34, 35 two-phase areas
36 three-phase area
M point of maximum solubility
$T_k$ crystallization temperature
A, B, C, D process points
A1, B1, C1, D1 process points (FIG. 5+FIG. 6)
A2, B2, C2, D2 process points (FIG. 6)
ΔT cooling The embodiments of the invention in which an exclusive property or privilege is claimed are defined as follows:

1. A method for racemate separation in compound-forming chiral substance systems, the method comprising:
    providing a fraction of a racemate enriched with an enantiomer;
    periodically performing preferential crystallizations on the enriched fraction or on another enriched fraction in accordance with a trajectory line of a eutectic plot of a ternary phase diagram to form a first crystal batch;
    measuring the composition with a mother liquor remaining in the fraction; and
    stopping the preferred crystallizations when the above measurements indicates departure from the trajectory line.

2. The method according to claim 1, wherein the second preferred crystallization is seeded with the racemate or the second enantiomer.

3. The method according to claim 1, wherein the second preferred crystallization is seeded with the racemate or the second enantiomer.

4. The method according to claim 1, wherein the enriched fraction is seeded with a first enantiomer greater than the eutectic composition.

5. The method according to claim 1, wherein enriching the fraction of the racemate is produced by a chromatographic method.

6. The method according to claim 1, wherein enriching the fraction of the racemate is produced using an enantioselective membrane.

7. The method according to claim 1, wherein enriching the fraction of the racemate is produced using supramolecular complexes.

8. The method according to claim 1, wherein stopping the first or the second preferred crystallizations occurs before nucleation of an undesired component.

9. The method according to claim 1, wherein the first enantiomer or the second enantiomer in combination with the racemate compound are obtained in an alternating manner.

10. The method according to claim 1, wherein measuring either the first enantiomer or the second enantiomer remaining in the racemate is undertaken in a batch or a continuous manner.

11. The method according to claim 1, wherein measuring either the first enantiomer or the second enantiomer remaining in the racemate includes at least one of polarimetric measurements, density measurements, and refractometric measurements.

* * * * *

UNITED STATES PATENT AND TRADEMARK OFFICE
CERTIFICATE OF CORRECTION

| | | |
|---|---|---|
| PATENT NO. | : 7,820,860 B2 | |
| APPLICATION NO. | : 12/064329 | |
| DATED | : October 26, 2010 | |
| INVENTOR(S) | : Seidel-Morgen-Stern et al. | |

It is certified that error appears in the above-identified patent and that said Letters Patent is hereby corrected as shown below:

Col. 9, please delete claim 3 as it is a duplicate of claim 2.

Signed and Sealed this
Fifteenth Day of February, 2011

David J. Kappos
*Director of the United States Patent and Trademark Office*

UNITED STATES PATENT AND TRADEMARK OFFICE
CERTIFICATE OF CORRECTION

PATENT NO. : 7,820,860 B2
APPLICATION NO. : 12/064329
DATED : October 26, 2010
INVENTOR(S) : Seidel-Morgen-Stern et al.

It is certified that error appears in the above-identified patent and that said Letters Patent is hereby corrected as shown below:

Delete the title page and substitute therefore the attached title page showing the corrected number of claims in patent.

Col. 9, lines 29-31, please delete claim 3 as it is a duplicate of claim 2.

This certificate supersedes the Certificate of Correction issued February 15, 2011.

Signed and Sealed this
Fifteenth Day of March, 2011

David J. Kappos
*Director of the United States Patent and Trademark Office*

(12) United States Patent
Seidel-Morgen-Stern et al.

(10) Patent No.: US 7,820,860 B2
(45) Date of Patent: Oct. 26, 2010

(54) METHOD FOR SEPARATING COMPOUND-FORMING CHIRAL SYSTEMS

(75) Inventors: Andreas Seidel-Morgen-Stern, Magdeburg (DE); Heike Lorenz, Magdeburg (DE); Daniel Polenske, Egeln (DE)

(73) Assignee: Max-Planck-Gesellschaft Zur Forderung Der Wissenshaften E.V., Egeln (DE)

(*) Notice: Subject to any disclaimer, the term of this patent is extended or adjusted under 35 U.S.C. 154(b) by 0 days.

(21) Appl. No.: 12/064,329

(22) PCT Filed: Aug. 17, 2006

(86) PCT No.: PCT/EP2006/065413
§ 371 (c)(1),
(2), (4) Date: Feb. 20, 2008

(87) PCT Pub. No.: WO2007/023129
PCT Pub. Date: Mar. 1, 2007

(65) Prior Publication Data
US 2008/0207944 A1 Aug. 28, 2008

(30) Foreign Application Priority Data
Aug. 20, 2005 (DE) .................. 10 2005 039 501

(51) Int. Cl.
*C07C 51/42* (2006.01)
(52) U.S. Cl. .................................................. 562/600
(58) Field of Classification Search .............. None
See application file for complete search history.

(56) References Cited

U.S. PATENT DOCUMENTS 5,260,482 A   11/1993   Pringle et al.

FOREIGN PATENT DOCUMENTS

| DE | 19536827 A1 |   | 4/1997 |
|----|----|----|----|
| EP | 0220435 | * | 5/1978 |
| EP | 0220435 A1 |   | 5/1987 |
| JP | 60202853 | * | 10/1985 |
| JP | 60202853 A |   | 10/1985 |
| WO | 199508522 A1 |   | 3/1995 |
| WO | 2007023129 A3 |   | 3/2007 |

OTHER PUBLICATIONS

"Pharmaceuticals, Chiral" in Kirk Othmer Encyclopedia of Chemical Technology, Copyright © 1996 by John Wiley & Sons, Inc., Article Online Posting Date: Dec. 4, 2000, pp. 1-49.*

Polenske, D, et al. (2006) Alternative Einsatzmoglichkeiten der "Bevorzugten Kristallisation" zur Enantiomerentrennung. Chemie Ingenieur Technik, 78(8):1101-10.

Elsner, M., et al. (2005) Experimental Study and Simplified Mathematical Description of Preferential Crystallization. Chirality, 17:S183-95.

Perlberg, A., et al. (2005) Crystal Growth Kinetics via Isothermal Seeded Batch Crystallization: Evaluation of Measurement Techniques and Application to Mandelic Acid in Water. Ind. Eng. Chem. Res., 44(4):1012-20.

Lorenz, H., et al. (2002) Enantiomeric Mandelic Acid System-Melting Point Phase Diagram and Solubility in Water. J. Chem. Eng. Data, 47(5):1280-84.

(Continued)

*Primary Examiner*—Karl J Puttlitz

(57) ABSTRACT

Methods for racemate separation for compound-forming substances. In this method, at least one fraction which is enriched with an enantiomer is produced in one method step. Finally, a preferred crystallization is carried out on the fraction.

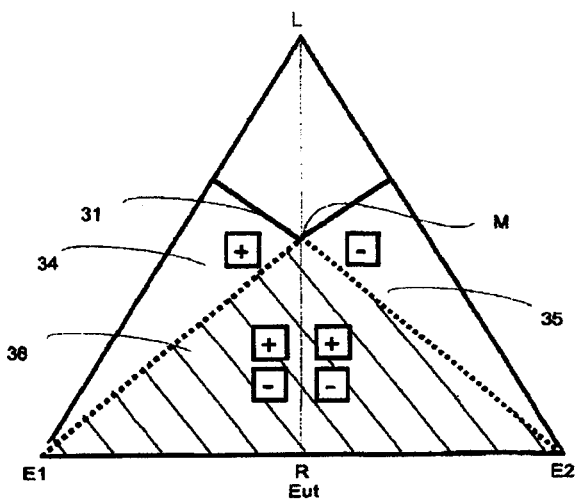

10 Claims, 4 Drawing Sheets